(12) United States Patent
McBeth

(10) Patent No.: US 7,896,497 B2
(45) Date of Patent: Mar. 1, 2011

(54) CORNEAL MEASUREMENT APPARATUS HAVING A SEGMENTED APERTURE AND A METHOD OF USING THE SAME

(75) Inventor: Jeffrey B. McBeth, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 329 days.

(21) Appl. No.: 11/954,160

(22) Filed: Dec. 11, 2007

(65) Prior Publication Data

US 2008/0151191 A1    Jun. 26, 2008

Related U.S. Application Data

(60) Provisional application No. 60/871,855, filed on Dec. 26, 2006.

(51) Int. Cl.
*A61B 3/10*    (2006.01)

(52) U.S. Cl. .................. 351/212; 351/211; 351/205

(58) Field of Classification Search .......... 351/205–246
See application file for complete search history.

(56) References Cited

U.S. PATENT DOCUMENTS

| | | | |
|---|---|---|---|
| 5,512,965 A | 4/1996 | Snook | 351/205 |
| 5,512,966 A | 4/1996 | Snook | 351/205 |
| 5,886,768 A * | 3/1999 | Knopp et al. | 351/212 |
| 6,286,958 B1 * | 9/2001 | Koest et al. | 351/214 |
| 6,575,573 B2 | 6/2003 | Lai et al. | 351/212 |
| 6,692,126 B1 | 2/2004 | Xie et al. | 351/212 |
| 7,275,827 B2 | 10/2007 | Jean | 351/212 |
| 2007/0188709 A1 * | 8/2007 | Saarloos et al. | 351/212 |

FOREIGN PATENT DOCUMENTS

| | | |
|---|---|---|
| WO | WO 02/45578 A1 | 6/2002 |
| WO | WO 03/032823 A2 | 4/2003 |
| WO | WO 2004/045400 A1 | 6/2004 |
| WO | WO 2006/015717 A1 | 2/2006 |

OTHER PUBLICATIONS

PCT/US2007/088311, "International Search Report and Written Opinion," Jun. 19, 2008.

* cited by examiner

*Primary Examiner*—Mohammed Hasan
(74) *Attorney, Agent, or Firm*—Jeffrey B. Powers

(57) ABSTRACT

An apparatus for measuring a subject's cornea having a mask subsystem disposed in a path of light from the light source, the mask subsystem configured to produce a segmented slits of the light.

28 Claims, 8 Drawing Sheets

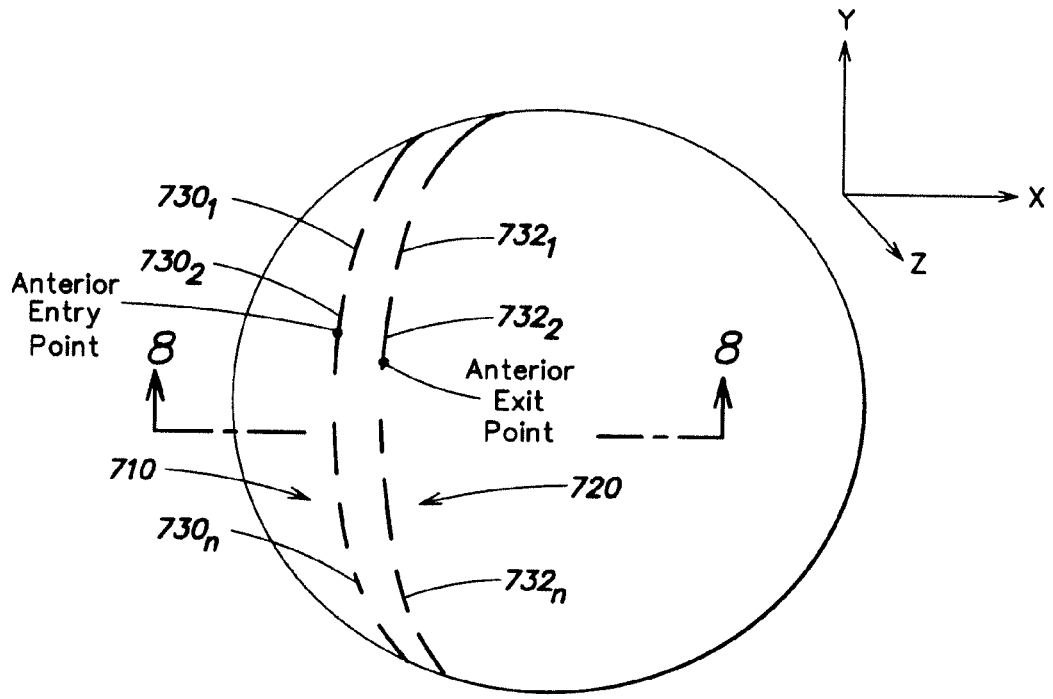
FIG. 7A
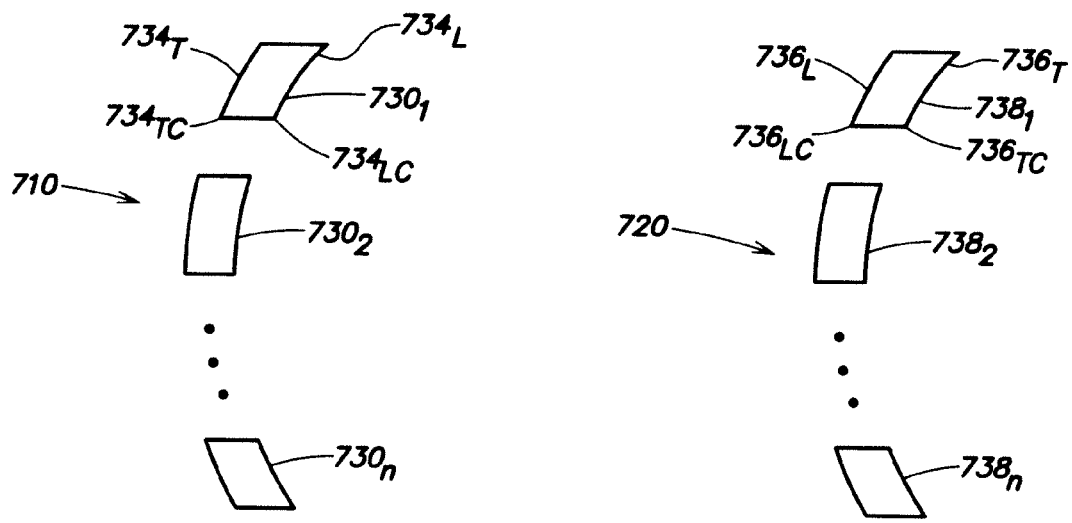
FIG. 7B  FIG. 7C

US 7,896,497 B2

CORNEAL MEASUREMENT APPARATUS HAVING A SEGMENTED APERTURE AND A METHOD OF USING THE SAME

CROSS-REFERENCE

This application claims the benefit of Provisional Patent Application No. 60/871,855 filed Dec. 26, 2006.

FIELD OF INVENTION

The present invention relates to corneal measurement apparatus and methods of corneal measurement, and more particularly to an apparatus and methods for projecting a plurality of segmented slits of light for performing corneal measurements.

BACKGROUND OF THE INVENTION

Ophthalmologists and optometrists would like to have an accurate representation of subjects' eye. Such representations include, for example, one or more of a representation of a subject's corneal anterior surface, posterior surface, and corneal thickness and density, as well as anterior chamber profiles. This information may be used to prescribe contact lenses and eye glasses, and to reshape the cornea by surgical procedures or to perform other surgical procedures. Since it is not comfortable to measure these data with physical contact, remote sensing techniques are preferably used to perform the measurements. A device that measures only the front surface of a cornea is commonly referred to as corneal topographer, a device that measures the front and back surfaces, and the stroma of the eye is referred to as a corneal profiler, and a device that measures anterior chamber profiles is called an anterior chamber analyzer.

One common technique for obtaining corneal measurement information includes projecting narrow bands of light (commonly referred to as slits or slit beams) onto a patient's cornea at multiple locations across a cornea. For each of the slits, after the light in the slit has been scattered by the cornea, an image of the light is obtained.

To project a slit of light, an aperture of appropriate shape and size, and a lens are placed in the path of light from a light source such that the light passing through the aperture forms a slit of light on a subject's cornea. Typically, to project slits at each of multiple locations across the cornea, a single aperture is translated such that the light passing through the aperture at selected times forms the multiple slits. One example of such a corneal measurement apparatus is presented in U.S. Pat. No. 5,512,966 to Snook.

A drawback with such apparatus is that it is difficult to accurately position an aperture to form each of the slits, and over time (after many patients) it is difficult to know the position of the slits accurately so that an accurate recreation of a cornea can be obtained. Another drawback of conventional apparatus is that it is difficult to characterize the back surface of a cornea due to the fact that a slit of light must pass through the anterior portion of a cornea, twice, before being imaged and analyzed.

SUMMARY

According to aspects of the present invention, a slit of light that is divided into segments is projected onto a cornea to facilitate characterization of the posterior surface of a cornea.

An aspect of the present invention is directed to an apparatus for measuring a subject's cornea, comprising (A.) an illumination projection subsystem comprising a light source, (B.) a mask subsystem disposed in a path of light from the light source, the mask subsystem configured to produce a segmented slit of the light, (C.) an imaging element configured and arranged to image the segmented slit of light onto the cornea, and (D.) an image capture subsystem arranged to capture images of the segmented slit of light after the segmented slit of light impinges on the cornea.

Another aspect of the invention is directed to a method of facilitating measurement of a subject's cornea, comprising (A.) projecting a segmented slit of light onto the cornea, (B.) imaging the segmented slit of light after it impinges on the cornea to form an image, and (C.) using at least two corners in the image to calculate a pathway of the light to the posterior surface of the cornea.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which:

FIG. 7A is a plan view of an eye illustrating the entry pathway and the exit pathway for a single segmented slit of light projected thereon;

FIG. 7B is an expanded plan view of the eye in FIG. 7A, illustrating the entry pathway of a segmented slit of light at the surface of the cornea;

FIG. 7C is an expanded plan view of the eye in FIG. 7A, illustrating the exit pathway of a segmented slit of light at the surface of the cornea

DETAILED DESCRIPTION

Aspects of the present invention are directed to an apparatus for measuring a subject's cornea, comprising an illumination projection subsystem comprising a light source, and a mask subsystem disposed in a path of light from the light source, the mask subsystem configured to produce a segmented slit of the light. An imaging element configured and arranged to image the segmented slit of light onto the cornea is also included. An image capture subsystem is arranged to capture images of the segmented slit of light after the segmented slit of light impinges on the cornea.

Figure 1:
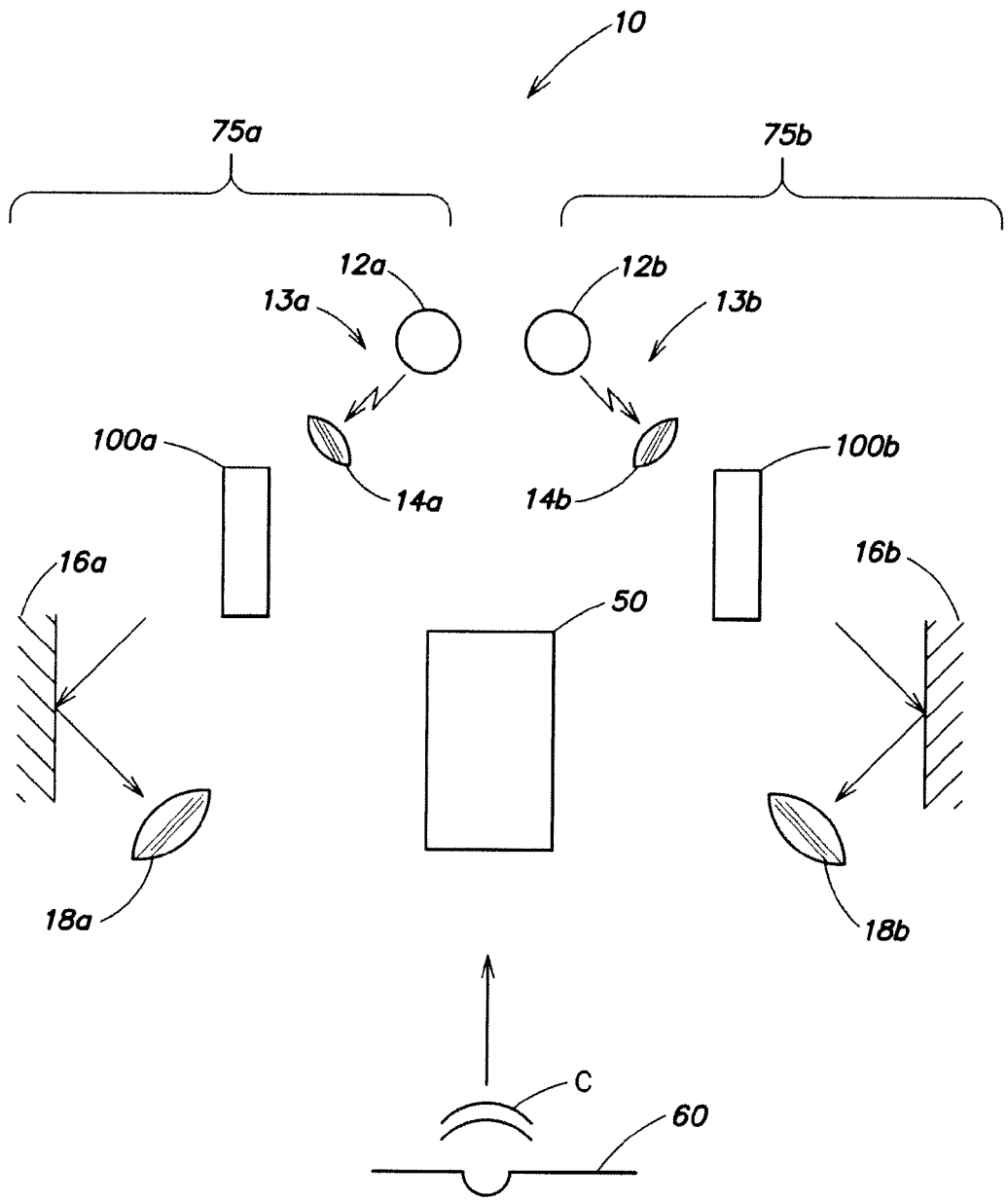
FIG. 1 is a schematic plan view of an example of a corneal measurement apparatus according to aspects of the present invention.

FIG. 1 is a schematic plan view of an embodiment of a corneal measurement apparatus 10 according to aspects of the present invention. The corneal measurement apparatus is adapted to measure a subject's cornea C. The corneal measurement apparatus comprises two illumination projection systems 13a, 13b (including light sources 12a and 12b, respectively), two mask subsystems 100a, 100b configured to produce one or more segmented slits of light, and an image capture subsystem 50. Mask subsystems 100a and 100b are disposed in the paths of light from illumination projection systems 13a and 13b, respectively.

Illumination projection system 13a and mask subsystem 100a are in a first arm 75a of the corneal measurement apparatus and illumination projection system 13b and mask subsystem 100b are in a second arm 75b of the corneal measurement apparatus. In the illustrated embodiment, the first arm projects slits of light onto one half of the cornea, and the second arm projects slits of light onto the other half of the cornea. For example, the path of the slits of light may be at a forty-five degree angle to the visual axis of the subject's eye. Although the illustrated embodiment of a measurement apparatus has two arms, in other embodiments, a measurement apparatus may only have a single arm.

Figure 2:
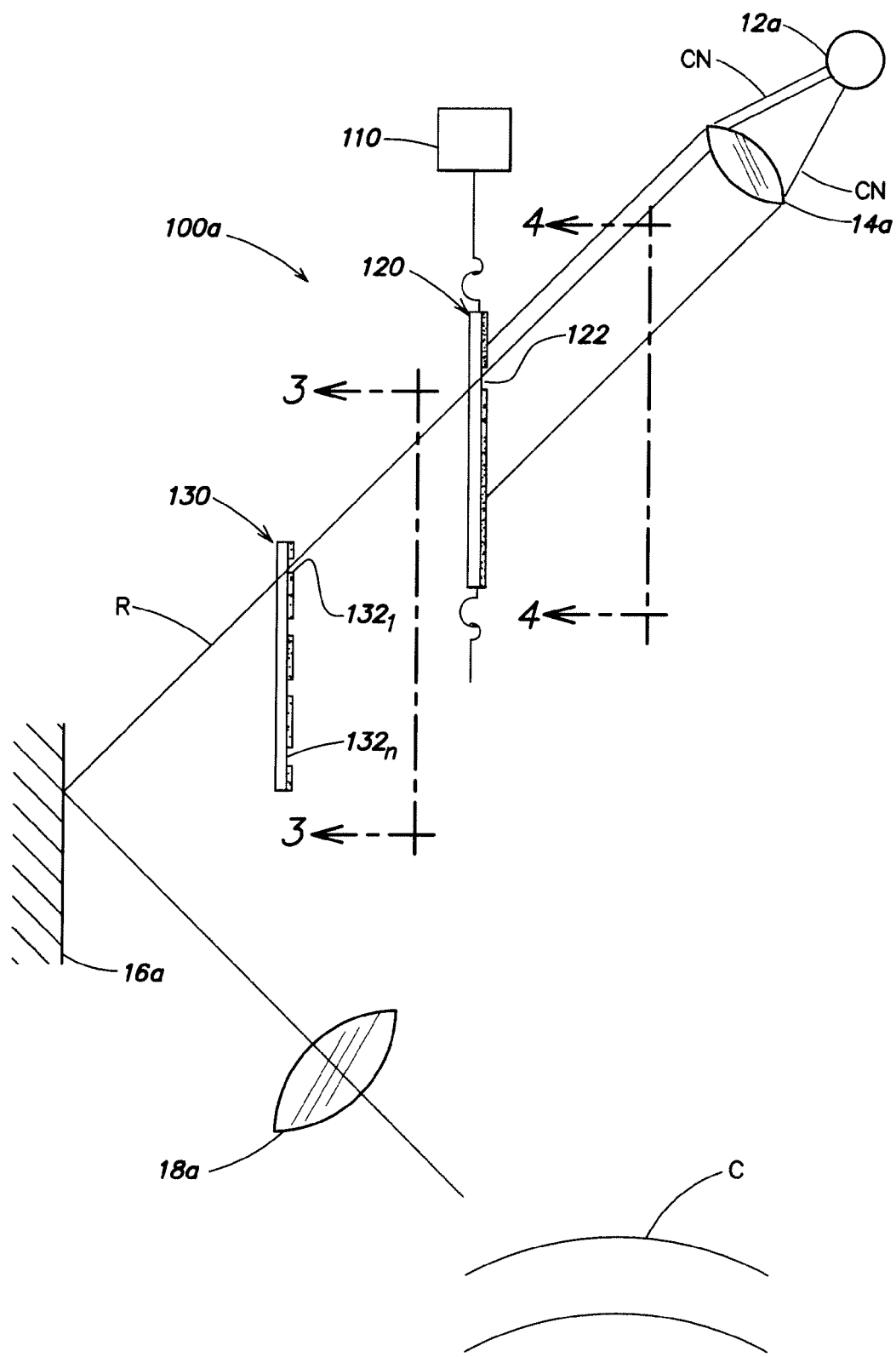
FIG. 2 is an expanded plan view showing further details of one arm of the corneal measurement apparatus of FIG. 1.

Referring to FIG. 2, further details of one arm of the corneal measurement apparatus 10 are shown. The arm comprises a first slit mask 130 defining a plurality of segmented apertures $132_i$ and a second slit mask 120 defining a selection aperture 122. The arm also comprises a translation apparatus 110 adapted to translate the second mask. Second slit mask 120 is configured and arranged such that, by appropriately positioning the second slit mask using the translation apparatus, selection aperture 122 selectively transmits portions of the light from source 12a such that light traveling through a selected one of the plurality of segmented apertures $132_i$ impinges on cornea C. Ray R demonstrates that the selection aperture 122 transmits light to cornea C from a selected one $132_1$ of the plurality of segmented apertures, when selection aperture 122 is appropriately aligned with the selected one $132_1$ of the plurality of segmented apertures. Subsequently, by translating second slit mask 120, the selection aperture can be positioned such that light from another of the plurality of segmented apertures $132_n$ can be transmitted to cornea C. Such positioning of the selection aperture can be repeated such that light from each of the plurality of segmented apertures or light from any suitable ones of the plurality of segmented apertures 132 can be transmitted to cornea C. It will be appreciated that, on portions of the first slit mask and the second slit mask that are outside of the apertures disposed thereon, the slit masks are opaque or substantially opaque to light from source 12a.

It is to be appreciated that although, in the illustrated embodiment, the second slit mask 120 (i.e., the mask including the selection aperture) is disposed upstream (i.e., closer to source 12a along the optical path) from first slit mask 130, in other embodiments, the first slit mask (i.e., the mask including the plurality of segmented apertures) can be disposed upstream of the second slit mask.

Referring again to FIG. 1, light sources 12a and 12b generate the light in which a corresponding mask subsystem is disposed. In some embodiments, the illumination projection system projects light from the light sources in a cone of light CN to permit light to be projected through each of the segmented apertures 132 defined in first slit mask 130 without moving the source or any other component in the illumination projection system. That is to say that, in some embodiments, only the second slit mask 120 is moved. The movement occurs to expose a given one of the plurality of segmented apertures on the second mask to light from a light source. It will be appreciated that, in such embodiments, the plurality of segmented apertures 132 that provide the slits of light can remain fixed in a given location during the acquisition of the plurality of slit images used to produce a representation of a subject's eye.

In some embodiments, it is advantageous if the source is monochromatic and suitably bright. For example, an LED or a plurality of LEDs may be used to generate the light. In some embodiments, a high power LED has been found useful. In some embodiments, a superluminescent LED is used. An aspect of the invention is directed to a single high power LED configured and arranged to be capable of illuminating the plurality of segmented apertures 132 as the selection aperture is moved.

In some embodiments, it is advantageous that the projection subsystem include a conventional condenser-projector system. In FIG. 1, condenser lenses 14a, 14b gather light from sources 12a and 12b respectively, and projector lenses 18a, 18b are configured and arranged such that the condenser lenses images sources 12a and 12b onto the projector lenses 18a, 18b, respectively. The projector lenses are also configured and arranged to image the apertures 132 onto cornea C. It is typically preferable that the slits of light are not convergent or divergent between the first slit mask and the cornea. However, some convergence or divergence may be present. Although in the illustrated embodiment the projectors 18a, 18b are lenses, any suitable imaging element may be used (e.g., a mirror, holographic element).

Although in the illustrated embodiment the condenser lenses 14a, 14b are illustrated as lenses, any suitable imaging element may be used (e.g., a mirror, holographic element). In some embodiments, the condenser lens may be omitted. The projection system components and first slit mask 130 may be disposed in a Scheimflug arrangement to obtain a plane of segmented slit images at cornea C. Also, one or more folding mirrors 16a and 16b may be included to direct light onto the cornea, and to achieve an appropriate package shape for a housing (not shown) of the apparatus.

Figure 3:
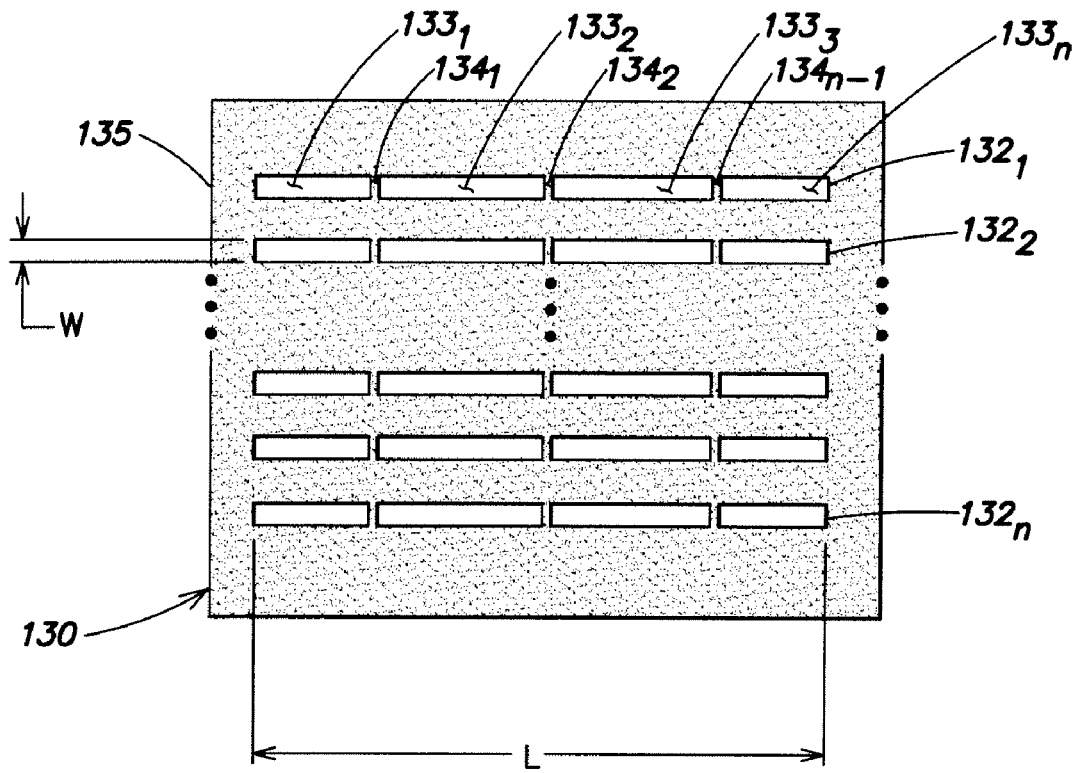
FIG. 3 is an illustration of an example of an embodiment of a first slit mask defining a plurality of segmented apertures viewed along line 3-3 of FIG. 2.

Further details of first slit mask 130 are now given with reference to FIG. 3. First slit mask 130 includes a plurality of segmented apertures $132_1$-$132_n$. Typically, the slits are of a same width W and length L and are evenly spaced apart; however, aspects of the invention are not so limited. Each of the apertures is divided into a plurality of segments $133_1$ to $133_n$. For example, to construct an aperture having a plurality of segments, one or more opaque divides $134_1$ to $134_{n-1}$ is provided in each of the apertures 132. However, the desired output is a segmented slit of light. Accordingly, a mask subsystem 100a, 100b may be constructed in any suitable way to provide a segmented slit of light. In some embodiments, a third mask may be provided in a mask subsystem that is disposed in a slit of light produced by rectangular slit (without divides) configured and arranged to produce segmented slits of light along a length corresponding to the direction of length L. In some embodiments, selection aperture 122 may be segmented such that the light projected therethrough is segmented before or after it passes through one of the plurality of apertures 132. Also, it is to be appreciated that for an aperture to be segmented or for a projection system to be configured to produce a segmented slit of light, the divides 134 may be less than completely opaque provided that they block enough light to produce an identifiable corners as described below with reference to FIG. 7B. Additionally, although the projection system described above is configured to produce rectangular slit segments of light, projection systems may be configured to produce slit segments of light that are other than rectangular. For example, the apertures 132 may be divided into square segments, or trapezoidal segments.

For example, twenty apertures may be provided on the slit mask in first arm 75a (shown in FIG. 1) so that twenty segmented slits of light are projected onto a subject's cornea and twenty images are obtained using light from the first arm 75a of the measurement apparatus 10 (shown in FIG. 1). Accordingly, when combined with twenty images from second arm 75b (shown in FIG. 1) a total of 40 slit images of a subject's eye are obtained. It will be appreciated that any suitable number of apertures 132 may be provided on the first slit mask in each of mask subsystems 100a, 100b (shown in FIG. 1). Each aperture 132 may be divided along its length L to facilitate measurement of the posterior surface of the cornea as described below.

For example, first slit mask 130 may be formed on a substrate 135 of soda lime glass or BK7 glass. An opaque layer may be deposited on a surface of the substrate. For example, an opaque metal layer may be deposited on the substrate, and the segmented apertures 132 may be subsequently formed by etching portions of the metal layer to expose the substrate. Each of the apertures has a length L and width W such that in a given measurement apparatus a segmented slit of light having a length L and width W is projected onto a cornea. Typically, the apertures are rectangular in shape. However, any suitable shape may be employed. In some embodiments, it may be desirable to apply and antireflective coating to one or both of the surfaces of a substrate. Although the plurality of segmented apertures 132 are shown as being formed on a single substrate (and in a single plane) any suitable construction may be used in which the apertures are formed at fixed locations relative to one another.

Figure 4:
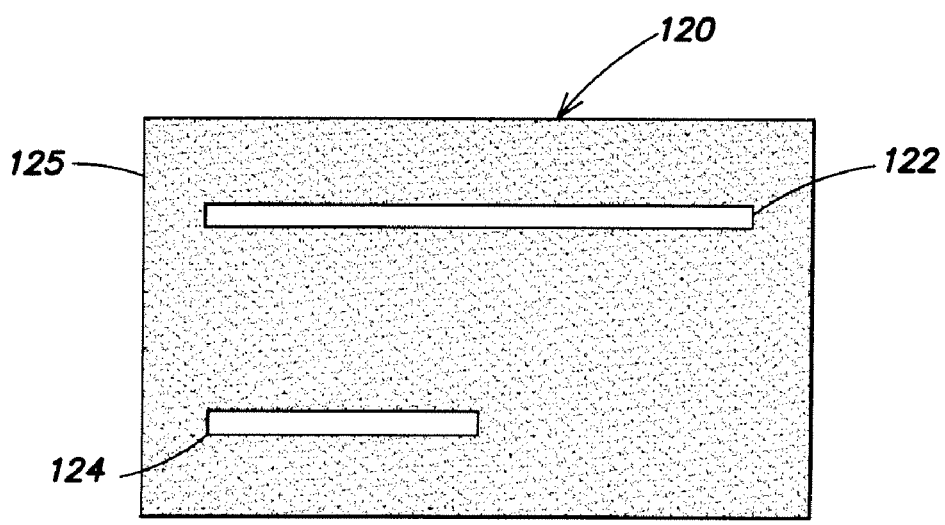
FIG. 4 is an illustration of an example of an embodiment of a second slit mask defining a selection aperture viewed along line 4-4 of FIG. 2.

Further details of the second slit mask 120 are now given with reference to FIG. 4. Second slit mask 120 includes a single selection aperture formed on a substrate 125. The selection aperture is sized to permit light to pass from one of the plurality of segmented apertures to cornea C (shown in FIG. 1). Typically, the size of the selection aperture is larger in width and length than any of the plurality of segmented apertures. The selection aperture is also typically small enough such that light is only permitted to pass through a single one of the plurality of segmented apertures and onto cornea C. A selection aperture is typically not segmented; however, as described above it may be segmented.

In the illustrated embodiment of the second slit mask, an aperture portion 124 (typically half the length of the selection aperture) is also provided. The aperture portion is used for alignment of the measurement apparatus relative to a subject's cornea on which a corneal measurement is to be made. The aperture portion is aligned with one of the plurality of segmented apertures on the first slit mask, such that light is projected though only a portion of the one of the plurality of segmented apertures and a portion of a slit of light is projected onto the middle of a subject's eye by the first arm 75a (shown in FIG. 1) (e.g., an upper half of a slit is formed at the middle of the subject's eye by the first arm).

Another, second slit mask 120 also having an aperture portion is disposed in the other arm 75b (shown in FIG. 1). Similar to the aperture portion in the first arm, the aperture portion in the second arm is aligned with one of the plurality of segmented apertures on the first slit mask of the second arm. Again, the aperture is arranged to project light onto the middle of the subject's cornea (e.g., a lower half of an aperture is formed at the middle of the subject's eye). In a conventional manner, the subject's cornea is aligned with the measurement apparatus, by positioning either the subject or the machine such that the two portions of the slits of light align to form a single, full-length (L) slit of light (e.g., the upper half of the slit of light from the first arm aligns with the lower half of the slit of light from the second arm) to form a single, full slit of light. The second slit masks 120 (in the first and second arm) may be formed in a manner similar to that described above for the first slit mask 130. The aperture portions are typically not segmented.

Referring again to FIG. 1, the image capture subsystem 50 is arranged to be able to capture an image of light projected for each of the plurality of segmented apertures after the light impinges on the cornea. It will be appreciated that, to capture the images to obtain a representation of a cornea, each of the plurality of segmented apertures is selected sequentially by appropriately aligning each segmented aperture with the selection aperture as described above. Light is projected through the segments of a given aperture 132 contemporaneously. Image capture subsystem 50 may be any suitable conventional imaging device, such as a CCD camera.

Translation apparatus 110 may comprise any suitable mechanism for translating the second slit mask 120 to project slits of light form the plurality of apertures 132 on the first slit mask 130 to cornea C. For example, the translation apparatus may comprise a linear translation motor capable of the moving the second slit mask in a direction perpendicular to the length L of the plurality of apertures 132.

Corneal measurement apparatus 10 also includes an image processing subsystem to convert the images into a single representation of the cornea. Techniques for reconstructing a representation of a subject's cornea once the slit images are obtained are well known and are not described further here. However, further details for using a segmented aperture to characterize the posterior surface of a cornea are given below. Projection systems as described herein may be used with cornea topographers, cornea profiler apparatus and anterior chamber analyzers.

Corneal measurement apparatus 10 includes a subject positioning apparatus 60 adapted to maintain a subject's cornea in a location. For example, the apparatus may be provided with a chin rest and/or a forehead rest which will fix the location of the subject's head.

Figure 5:
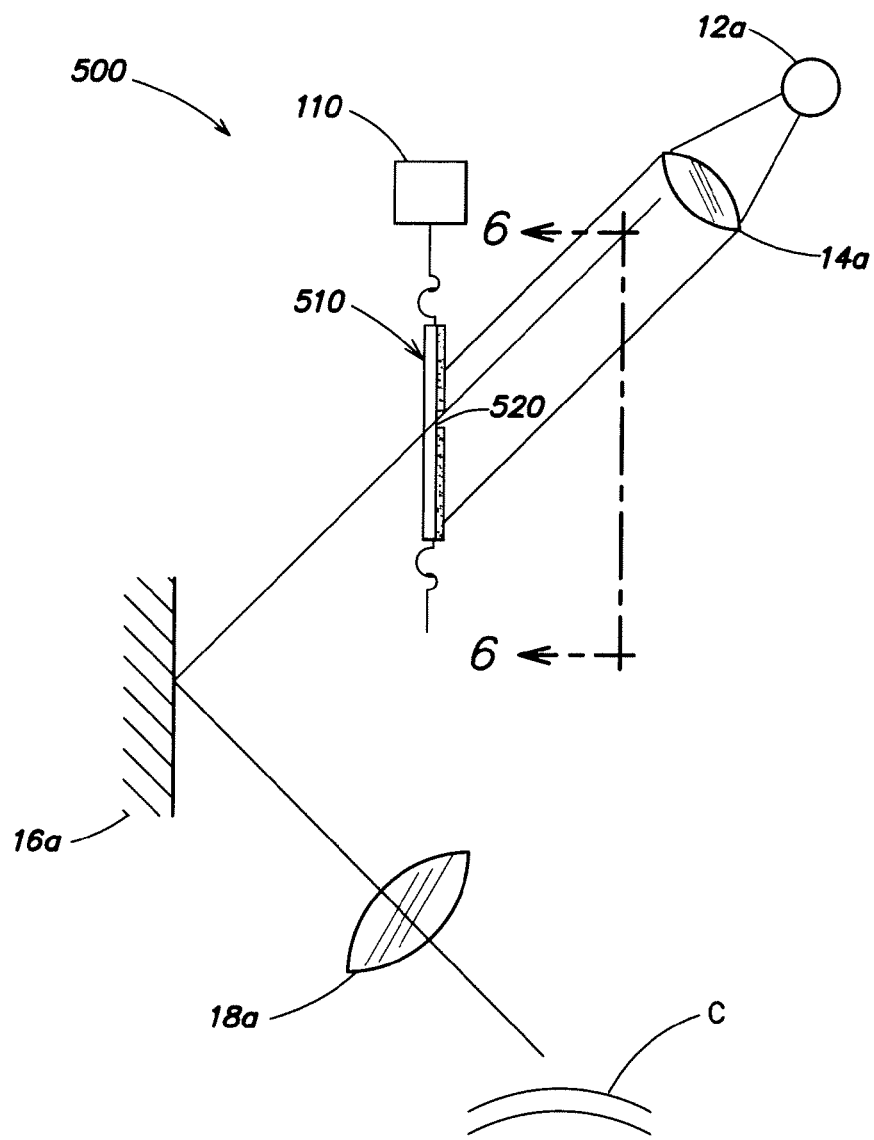
FIG. 5 is an expanded plan view showing an alternative embodiment of one arm of the corneal measurement apparatus of FIG. 1.

FIG. 5 is an expanded plan view showing an alternative embodiment of one arm 500 of the corneal measurement apparatus of FIG. 1. Arm 500 is the same as the arm in FIG. 2 except as disclosed here. Arm 500 comprises a mask subsystem comprising a first slit mask 510 having a single aperture 520 configured to produce segmented slits of light. First slit mask 510 is coupled to a translation apparatus 110 that translates the mask to produce a plurality of slits at different location on cornea C. There is no selection mask in arm 500.

Figure 6:
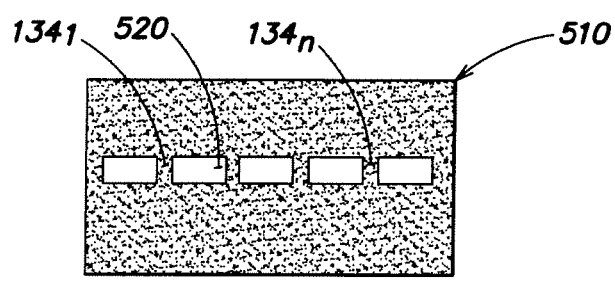
FIG. 6 is an illustration of an alternative embodiment of a first slit mask defining a single segmented aperture viewed along line 6-6 of FIG. 5.

FIG. 6 is a plan view of the first slit mask 510 of FIG. 5 viewed along line 6-6 of FIG. 5. First slit mask 510 includes a single segmented aperture 520 having a plurality of divides $134_1$-$134_n$.

Although the embodiments illustrated in FIGS. 2 and 5 are constructed to translate a slit mask having segmented aperture, it will be appreciated that aspects of the present invention may be used with apparatus that are constructed to move such slit masks in other manners. For example, such slit masks may be used in an apparatus constructed to rotate the slit mask about an axis. Examples of such apparatus are given in U.S. Pat. No. 4,171,877 to Karasawa and U.S. Pat. No. 6,286,958 to Koest.

FIGS. 7A-9B are schematic illustrations of light projected from a segmented aperture according to aspects of the invention. The light may be from one aperture of a first slit mask having plurality of apertures as described above with reference to FIG. 3 or may be from a first slit mask having only a single aperture as described with reference to FIG. 6.

FIG. 7A is a plan view of an eye illustrating an entry pathway 710 and an exit pathway 720 of a single segmented slit of light projected thereon. The slit of light has a plurality of segments of light $730_1$-$730_n$ at its entry pathway and a plurality of segments of light $732_1$-$732_n$ at its exit pathway. The slit of light enters the eye along a line that intersects the curved cornea and therefore forms a curved line of illumination at the entry location.

FIG. 7B is an expanded plan view of the eye in FIG. 7A, illustrating the entry pathway 710 of a segmented slit of light having segments $730_1$-$730_n$ at the surface of the cornea. The segments have a leading edge $734_L$ (the right side) and a trailing edge $734_T$ (the left side), and a leading corner $734_{LC}$ and trailing corner $734_{TC}$.

FIG. 7C is an expanded plan view of the eye in FIG. 7A, illustrating the exit pathway of a segmented slit of light having segments $738_1$-$738_n$ at the surface of the cornea. The segments have a trailing edge $736_T$ (the right side) and a leading edge $736_L$ (the left side), and a trailing corner $736_{TC}$ and leading corner $736_{LC}$.

Figure 8:
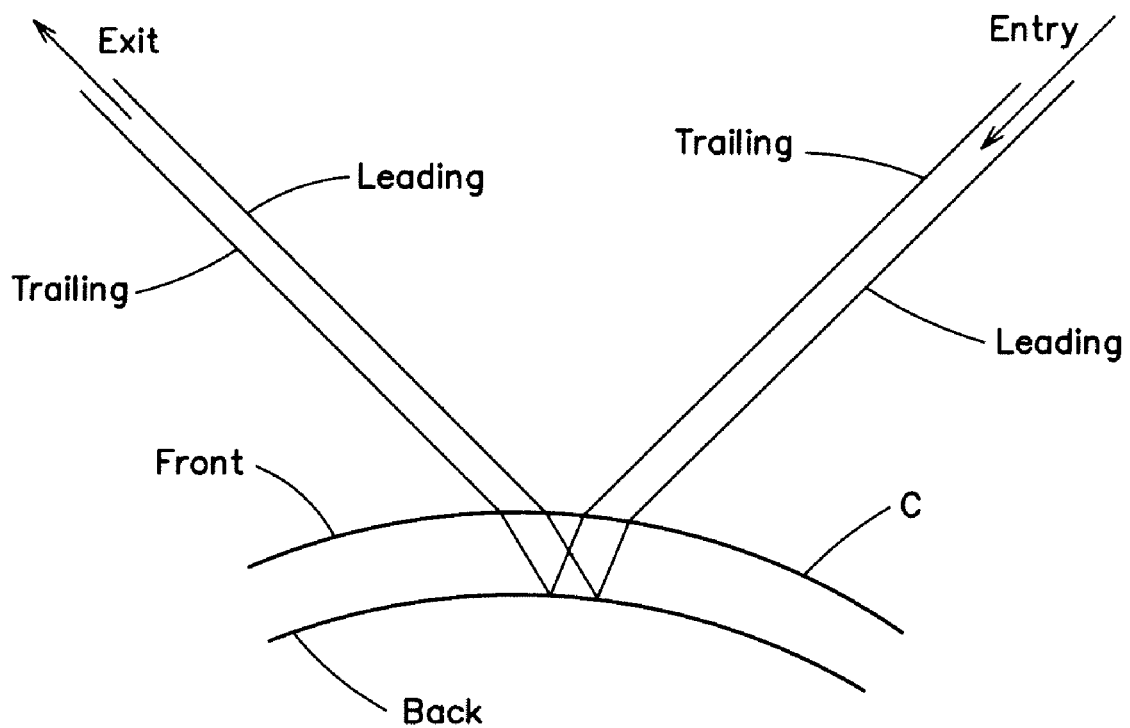
FIG. 8 is a cross sectional view of the eye taken along line 8-8 of FIG. 7 showing the entry pathway and the exit pathway of the slit of light.

FIG. 8 is a cross sectional view of the eye taken along line 8-8 of FIG. 7A showing the entry pathway and the exit pathway of the slit of light. The view illustrates a cross section of one segment of the segmented slit of light. The view illustrates light entering the cornea C, reflects from the posterior surface of the cornea, and exits the cornea.

Figure 9A:
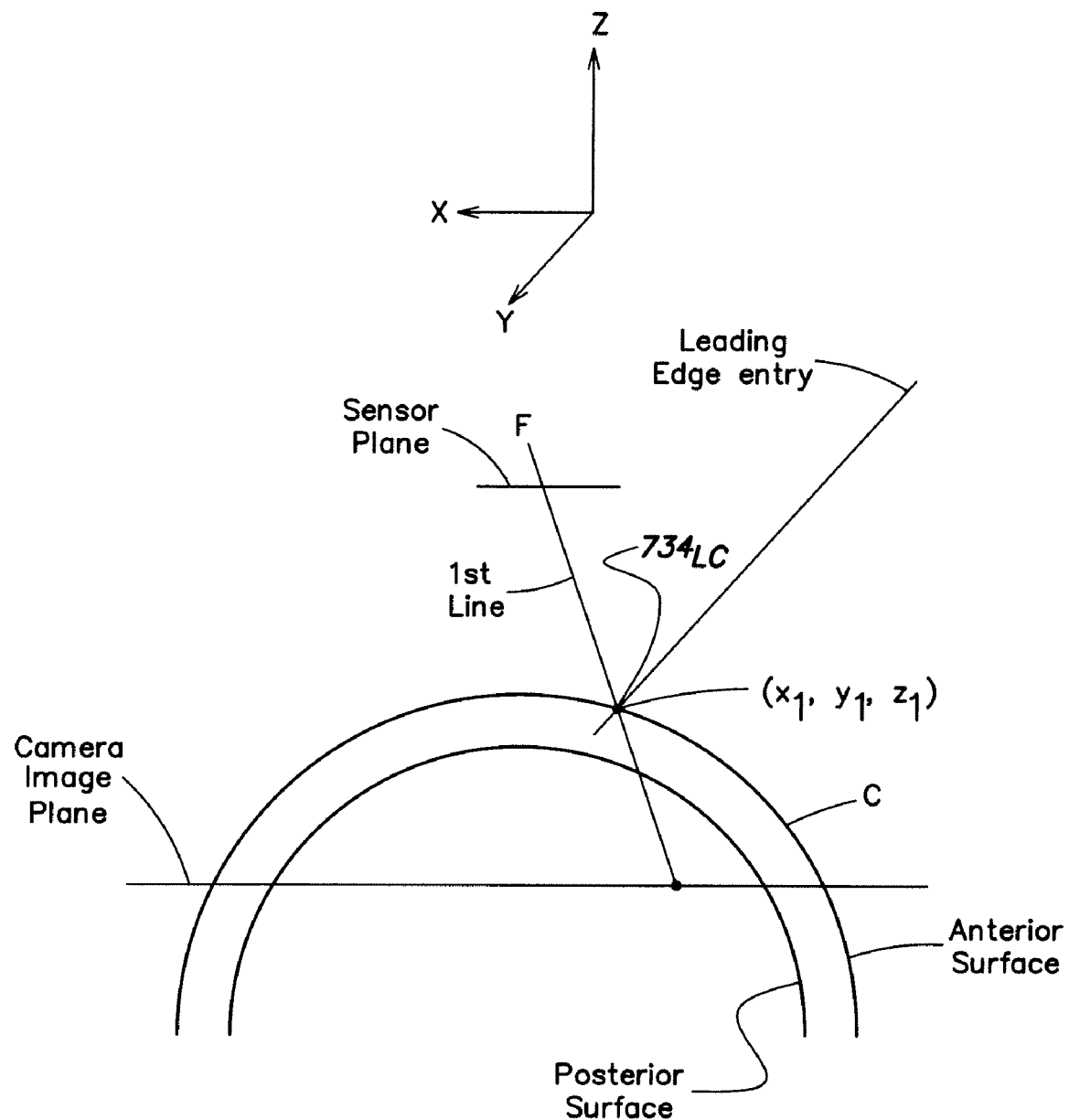
FIGS. 9A and 9B are a cross sectional views of the eye as shown in FIG. 8 including features relevant for measuring the posterior surface of the eye.
Figure 9B:
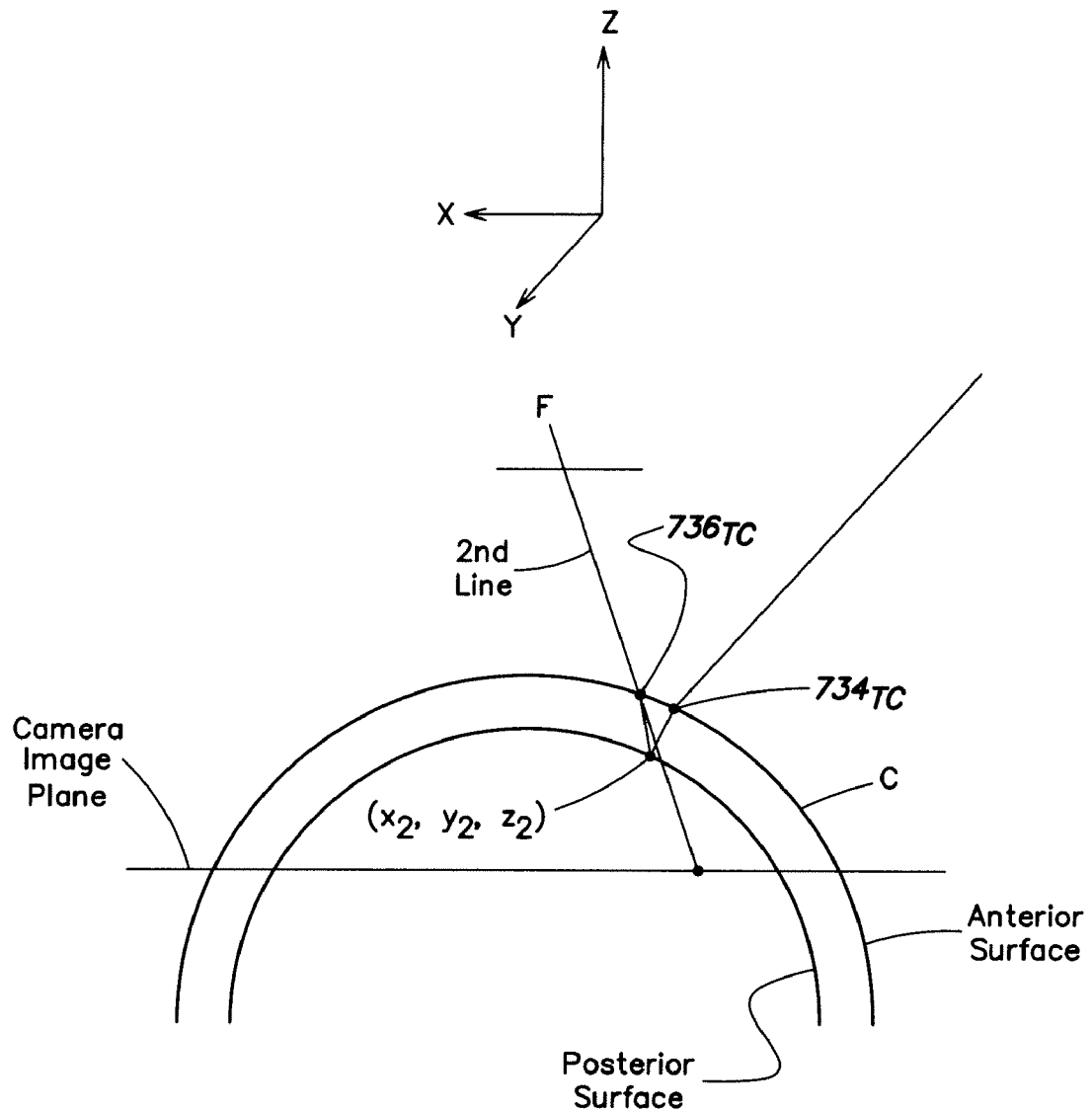

FIGS. 9A and 9B are cross sectional views of the eye as shown in FIG. 8 including features relevant for measuring the posterior surface of the eye. For simplicity, only a leading edge entry ray for a leading corner point $734_{LC}$, a trailing edge entry ray for a corner point $734_{TC}$, and the trailing edge exit corner point $736_{TC}$ are illustrated in FIGS. 9A and 9B. It is to be appreciated that the above points are shown as being on the surface of the cornea in a single cross section for simplicity. It is to be further appreciated that any of the above points can have any location in three-dimensional (3-D) space as determined by a subject's cornea. Although calculations for only bottom corners of given segment are discussed below, upper corners of a segment may also be used.

The following discussion presents one example of a calculation technique using light projected from a segmented aperture. Any suitable calculation technique may be used with segmented apertures according aspects of the present invention.

Prior to measurement of an eye the following information is known relative to the sensor plane of the camera in the image capture subsystem 50 (shown in FIG. 1):

1.) the distance to the camera image plane

2.) the location of the focal point F (also commonly referred to as the vanishing point) of the camera. Any known technique may be used to determine the location of focal point F.

2.) the paths of the entry rays (including the rays corresponding to the corners (e.g., corner $734_{LC}$)) are known prior to the measurement of eye. Any suitable technique of determining the path of ray of light may be used. For example, diffusely reflective surfaces, as described in U.S. patent application Ser. No. 11/610,059, titled Optical Calibration System and Method, filed Dec. 13, 2006, by Lai et al may be used. Said application is hereby incorporated by reference.

Calculations and measurements are performed as follows.

A. Determine the Topography of the Anterior Surface of the Cornea.

Referring to FIG. 9A, the location in 3-D space of the entry point corresponding to the corners of the leading edges of the segments of light are determined.

I. A first point on the CCD corresponding to the leading edge entry corner $734_{LC}$ is determined using conventional edge detection techniques.

II. A first line is determined that runs through the focal point F and the first point.

III. An intersection of the first line with the path of the entry ray of leading edge entry ray for corner point $734_{LC}$ (known a priori) is calculated. The ray and the first line may not intersect due to artifacts of the discrete (or pixelized) nature of the digital image, or due to calibration estimations, etc. In the absence of an intersection between the first line and the leading edge entry ray, the location of closest-passing of the lines is selected as entry point $(x_1, y_1, z_1)$ of the leading edge.

III. When all of the entry points at the anterior surface (corresponding to all slit locations) are identified, a surface is fit to the plurality of entry points. For example, a surface may be fit using a non-uniform rational basis surface (NURB), a cubic spline, or simply fitting a spherical surface. A normal at any location on the anterior surface is then calculateable.

B. Trace an Entry Ray Corresponding to Trailing Edge Entry Ray.

I. Given that the shape of the aperture is known and a ray corresponding to the leading edge entry ray for corner point $734_{LC}$ is also known, a ray corresponding to the trailing edge entry ray for corner point $734_{TC}$ is calculated (shown in FIG. 9B).

II. Snell's law is applied using knowledge of the surface normal (calculated above) and the path of the trailing edge entry ray for corner point $734_{TC}$ to determine the direction of the trailing edge after the ray passes through the anterior surface of the cornea.

C. Determine the Location in 3D Space of the Exit Point of the Trailing Edge.

I. A second point on the CCD corresponding to trailing edge exit corner point $736_{TC}$ is determined using conventional edge detection techniques.

II. A second line is established that runs through the focal point F and the second point.

III. Snell's law is applied using knowledge of the surface normal of the anterior surface of the cornea (calculated as above) and the second line to determine the direction of the trailing edge exit ray corresponding to corner point $736_{TC}$ inside the anterior surface of the cornea.

D. Determine the Shape of the Cornea.

I. An intersection of the trailing edge entry ray corresponding to corner point $734_{TC}$ after passing through anterior surface of the cornea, and knowledge of the direction of the trailing edge exit ray corresponding to corner $736_{TC}$ inside the anterior surface of the cornea are used to determine a point of reflection on the rear surface of the cornea $(x_2, y_2, z_2)$. However, the trailing edge entry ray inside the cornea and the trailing edge exit ray inside the cornea may not intersect due to artifacts of the discrete (or pixelized) nature of the digital image, or due to calibration estimations, etc. In the absence of an intersection, the location of closest passing of the two rays is selected as the point of reflection $(x_2, y_2, z_2)$ of the leading edge.

II. When all of the points of reflection have been identified, a surface is fit to plurality of surfaces that represents the posterior surface of the cornea. For example, a surface may be fit using a non-uniform rational basis surface (NURB), a cubic spline, or simply fitting a spherical surface. A normal at any location on the anterior surface is then calculateable.

It should be appreciated that calculation of the shape of the posterior surface of the cornea was facilitated by projecting segments of a slit of light because the exit rays and the entry rays that are to be intersected to determine the location of the posterior surface at a given point are readily identifiable (i.e., they are located at the corners). That is, the entry ray corresponding to a given trailing corner of a segment is assumed to intersect the exit ray corresponding to the same trailing corner. A continuous slit (i.e., a slit with out segments) provides no such advantage.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An apparatus for measuring a subject's cornea, comprising:
   (A.) an illumination projection subsystem comprising a light source;
   (B.) a mask subsystem disposed in a path of light from the light source, the mask subsystem configured to produce a segmented slit of the light;
   (C.) an imaging element configured and arranged to image the segmented slit of light onto the cornea; and
   (D.) an image capture subsystem arranged to capture images of the segmented slit of light after the segmented slit of light impinges on the cornea.

2. The apparatus in claim 1, wherein the mask subsystem comprises a first slit mask having comprising a segmented aperture.

3. The apparatus in claim 1, wherein the mask subsystem comprises a first slit mask consisting of only a single segmented aperture.

4. The apparatus in claim 1, wherein the segmented aperture is configured to produce rectangular segments of light.

5. The apparatus of claim 2, further comprising a translation apparatus adapted to translate the first slit mask.

6. The apparatus of claim 1, further comprising:
   (E.) a second illumination projection subsystem comprising a second light source; and
   (F.) a second mask subsystem disposed in a path of second light from the second light source, the second mask subsystem configured to produce a segmented slit of the second light.

7. The apparatus of claim 1, wherein the mask subsystem comprises a first slit mask defining a plurality of apertures.

8. The apparatus of claim 7, wherein the mask subsystem further comprises, a second slit mask defining a selection aperture, and
   a translation apparatus adapted to translate the second slit mask, the translation apparatus and the second slit mask being configured and arranged such that by translating the selection aperture, portions of the light can be selectively transmitted through ones of the plurality of apertures toward the cornea, sequentially.

9. The apparatus of claim 8, wherein the second slit mask is configured to produce the segmented slit of the light.

10. The apparatus in claim 1, wherein the light source comprises at least one LED arranged to project light in the path of light.

11. The apparatus in claim 1, further comprising a condenser lens configured and arranged to gather light from the light source and project the light in the path of light.

12. The apparatus in claim 11, wherein the imaging element and the condenser lens are configured and arranged to operate as a condenser-projector system.

13. The apparatus in claim 7, wherein the imaging element and the first slit mask are disposed in a Scheimflug arrangement to obtain a plane of slit images at the cornea.

14. The apparatus in claim 7, wherein the plurality of apertures are disposed in a single plane.

15. The apparatus in claim 14, wherein the plurality of apertures are formed on a single substrate.

16. The apparatus in claim 15, wherein the plurality of apertures is defined by openings in an opaque layer deposited on the substrate.

17. The apparatus in claim 1, further comprising an image processing subsystem coupled to the image capture subsystem, the image processing subsystem being adapted to convert a plurality of images into a single representation of the cornea.

18. The apparatus in claim 1, further comprising a subject positioning apparatus adapted to maintain the subject's cornea in a location.

19. The apparatus in claim 7, wherein the light source comprises at least one high power LED.

20. The apparatus in claim 19, wherein the light source consists of a single LED.

21. A method of facilitating measurement of a subject's cornea, comprising:
   (A.) projecting a segmented slit of light onto the cornea by projecting light from a light source through a slit mask;
   (B.) imaging the segmented slit of light after it impinges on the cornea to form an image; and
   (C.) using at least two corners in the image to calculate a pathway of the light to the posterior surface of the cornea.

22. The method of claim 21, wherein the step of projecting comprises projecting light through a first slit mask comprising a segmented aperture.

23. The method of claim 21, wherein the step of projecting comprises projecting light through a first slit mask comprising a first slit mask consisting of only a single segmented aperture.

24. The method of claim 21, wherein the step of projecting comprises projecting light to produce rectangular segments of light.

25. The method of claim 21, further comprising translating the first slit mask.

26. The method of claim 21, wherein the step of projecting comprises projecting light through a first slit mask defining a plurality of apertures.

27. The method of claim 26, further comprising translating a selection aperture to selectively transmit light through ones of the plurality of apertures toward the cornea, sequentially.

28. The method of claim 21, further comprising converting a plurality of images into a single representation of the cornea.

* * * * *